United States Patent [19]

Outmans

[11] Patent Number: 4,586,376
[45] Date of Patent: May 6, 1986

[54] DETERMINING THE EFFECT OF FLUID FLOW THROUGH PERMEABLE MEDIA

[75] Inventor: H. Donald Outmans, Laguna Beach, Calif.

[73] Assignee: Union Oil Company of California, Los Angeles, Calif.

[21] Appl. No.: 654,761

[22] Filed: Sep. 25, 1984

[51] Int. Cl.$^4$ ..................... G01N 15/08; G01N 33/24
[52] U.S. Cl. ..................................... 73/432 R; 73/38
[58] Field of Search .............. 73/432 Z, 432 R, 432 J, 73/38, 153

[56] References Cited

U.S. PATENT DOCUMENTS

| | | | |
|---|---|---|---|
| 2,733,595 | 2/1956 | Twining | 73/38 |
| 3,018,660 | 1/1962 | Schmid | 73/38 X |
| 3,027,752 | 4/1962 | Parnell | 73/38 |
| 3,358,755 | 12/1967 | Chisolm | 166/264 |
| 3,405,553 | 10/1968 | Boisard et al. | 73/38 |
| 3,420,093 | 1/1969 | Collins | 73/38 |
| 4,247,298 | 1/1981 | Rippie | 73/432 Z X |
| 4,253,327 | 3/1981 | Wiley | 73/38 |
| 4,304,122 | 12/1981 | Tentor | 73/153 X |
| 4,458,520 | 7/1984 | Adame et al. | 73/432 R X |
| 4,482,634 | 11/1984 | Davis, Jr. et al. | 73/153 X |
| 4,486,714 | 12/1984 | Davis, Jr. et al. | 73/153 X |
| 4,487,056 | 12/1984 | Wiley | 73/38 |
| 4,501,143 | 2/1985 | Prior et al. | 73/153 |

FOREIGN PATENT DOCUMENTS

| | | | |
|---|---|---|---|
| 2057343 | 5/1971 | France | 73/432 Z |
| 135060 | 1/1961 | U.S.S.R. | 73/38 |
| 139635 | 9/1961 | U.S.S.R. | 73/38 |
| 548822 | 4/1977 | U.S.S.R. | 73/38 |
| 794434 | 1/1981 | U.S.S.R. | 73/38 |
| 996941 | 2/1983 | U.S.S.R. | 73/432 R |

OTHER PUBLICATIONS

"On-Site Testing to Define Injection-Water Quality Requirements" by C. C. McCune *Journal of Petroleum Technology,* Jan. 1977, pp. 17-24.
"Abstract-Chevron Plans for On-Site Sampling and Analyzing of Geothermal Waters," by W. S. Subcasky, *Proceeding of the Second Work Shop on Sampling and Analysis of Geothermal Effluents* Held at Las Vegas, NV, Feb. 15-17, 1977, U.S. Department of Commerce National Technical Information Service, Jun. 1978, p. 43 and 2 Drawing Figures.
"Permeability Changes During the Flow of Water Through Westerly Granite at Temperatures of 100°-400° C." by R. Summers, K. Winkler, and J. Byerlee *Journal of Geophysical Research,* vol. 83, No. B1, Jan. 10, 1978, pp. 339-344.

Primary Examiner—Stewart J. Levy
Assistant Examiner—Tom Noland
Attorney, Agent, or Firm—Dean Sandford; Gregory F. Wirzbicki; June M. Bostich

[57] ABSTRACT

A method and apparatus for determining the effect of the flow of a fluid through a permeable particulate medium wherein a sample of the fluid is maintained as nearly as possible in the same physical and chemical condition as when it is sampled and is uniformly aged before being passed through a permeable particulate test medium. Some property of the sample, or of the permeable particulate test medium, such as a flow characteristic, is measured to determine the effect of passing the fluid through the permeable medium.

52 Claims, 1 Drawing Figure

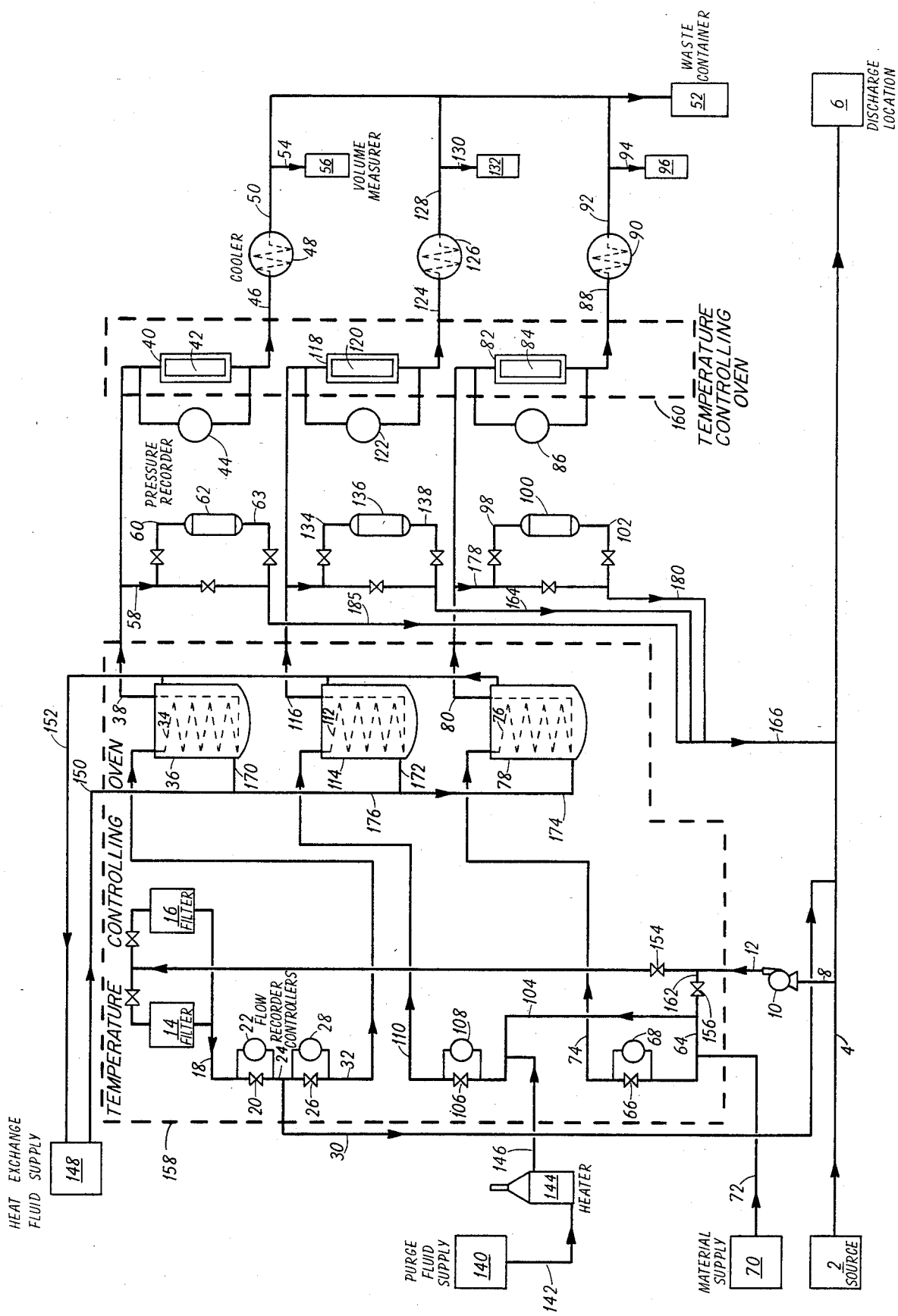

DETERMINING THE EFFECT OF FLUID FLOW THROUGH PERMEABLE MEDIA

BACKGROUND OF THE INVENTION

1. Field of the Invention

The invention relates to a method and apparatus for determining the effect of the flow of a fluid through a permeable particulate medium. More particularly, the invention relates to such a method and apparatus wherein a stream of such fluid is to be passed into a permeable particulate medium as part of an industrial operation.

2. Description of the Prior Art

In many industrial operations a fluid is passed into a permeable particulate medium. Such operations include processes wherein the fluid is filtered or disposed of, or its flow characteristics are altered. During each of these operations changes can occur in the fluid, in the permeable particulate medium or in the conditions of flow. Since these changes can raise difficulties in the transfer of fluids, it is desirable to evaluate them in some manner short of carrying the full scale operation to completion. In this way the results of each process can be more readily predicted. Such testing is particularly important when dealing with processes wherein the permeable medium or the fluid is not readily available for observation or examination due to its remote or inaccessible location.

In certain industrial operations involving flow through a permeable medium, the fluids are onerous to handle because of their composition or physical characteristics. More particularly, the process may involve fluids at elevated temperature or pressure, such as fluids to be injected into a subterranean reservoir penetrated by a well. Examples of such operations are enhanced oil recovery or reinjection into a geothermal reservoir of spent brine produced for use in power generation. Since in such operations the permeable particulate medium is the reservoir rock penetrated by a well, the medium is not readily accessible for examination during the period of reinjection. As a result, the effect of the reinjected fluid upon the reservoir formation is difficult to determine directly. The reservoir can become plugged by precipitation of constituents from the reinjected fluid or by reaction products of the reservoir rock and the fluid. If the permeability of the reservoir is altered in any way by contact with the reinjected fluids, the ability of the reservoir to accept fluid can be seriously impaired.

It has been proposed previously to sample a fluid and test the effect of its passage into a permeable porous medium. Summers, et al. in "Permeability Changes During the Flow of Water Through Westerly Granite at Temperatures of 100°–400° C.", *Journal of Geophysical Research*, Vol. 83, No. B1, Jan. 10, 1978, pp. 339 to 344, describe a method of determining how permeability will change with time when water is circulated through a fracture system in hot rock. To determine the effect of the circulating water, granite cylinders were placed in a sleeve under a confining pressure and heated. Water was then flowed through the rock for up to 17 days. Examination of the rock showed some changes, for example, the deposition of aluminum silicates and significant reductions in permeability.

U.S. Pat. No. 3,420,093 to Collins describes a method and apparatus for measuring a change in permeability of an earthen or rock formation wherein the rate of flow of a test liquid through a core of the formation is maintained as nearly constant as possible throughout the test period by adjusting a pressure relief valve as the permeability increases or decreases. The core is contained in a Hassler sleeve. The invention can be used to study the action of a test fluid which tends to plug the existing channels of the formation.

A method and apparatus for on-site testing of the effect of waterflood injection water on formation core permeability is described by McCune in "On-Site Testing to Define Injection-Water Quality Requirements," *Journal of Petroleum Technology*, January, 1977, pp. 17 to 24. Test cores are sealed in aluminum tubes with epoxy resin and immersed in a stirred constant temperature bath. Injection water from a sample bomb is forced through the core and the flow rate is measured. Various chemicals, such as scale inhibitors, chelating agents and sequestering agents can be added to the injection water so that the effect of such additives on the cores can be determined. However, the disadvantage of this method and apparatus is that the fluid sample does not necessarily have the same chemical and physical condition at its point of entry into the permeable test medium as the main body of the injection fluid has upon its entry into the well. Unless the sample stream is aged without backmixing while being maintained at wellhead injection temperature and pressure, the sample cannot truly represent the fluid stream and, hence, cannot reliably predict the effect of injection upon the permeability of the reservoir.

While the above-described methods and apparatus have met with some success, a need remains for an improved method and apparatus for determining the effect of the flow of a fluid into a permeable particulate medium. For example, the need exists for an on-site test apparatus and process whereby a sample is withdrawn from a fluid stream and passed into a permeable test medium while having the same temperature, pressure and uniform age between the point of sampling and the point of injection as the main body of the fluid stream.

Accordingly, it is a principal object of this invention to provide such a method and apparatus wherein the condition of the sample fluid throughout the procedure is maintained as nearly as possible the same as when it was sampled.

It is a further object of the invention to provide such method and apparatus wherein the sample fluid is uniformly aged after sampling but before it enters the permeable particulate test medium.

It is a still further object of the invention to provide such a method and apparatus wherein the time of aging corresponds to the length of time required for passage of the main body of the fluid between the sampling point and the point of injection into a permeable particulate medium in an industrial operation.

It is another object of the invention to provide such a method and apparatus wherein a continuously sampled fluid is maintained at a uniform age, i.e., aging is achieved without backmixing with fluid more recently or previously sampled.

Yet another object of the invention is to provide such a method and apparatus wherein scale formation in the test equipment exposed to the test fluid during test start up or shut down is minimized.

Other objects, advantages and features of the invention will become apparent from the following description, drawing, and appended claims.

SUMMARY OF THE INVENTION

Briefly, the invention involves a method and apparatus for determining the effect of the flow of a fluid through a permeable particulate medium wherein a body of the fluid is sampled, and the sample is maintained throughout the operation as nearly as possible at the same conditions of temperature and pressure as when sampled. At the same time, the sample is uniformly aged without backmixing for a period of time corresponding to the time necessary for the main body of the fluid to travel between the sampling point and the point of injection into a permeable particulate medium so that the sample entering a permeable test medium is substantially the same age as the main body of the fluid stream when it is passed into a permeable medium during industrial processing. The effect of the fluid upon the permeable particulate medium is determined by measuring a flow characteristic of the system, or some property of the fluid sample or of the permeable test medium. Optionally, a treating material is blended into the fluid sample prior to passing the same through the core.

The flow test apparatus of this invention includes in fluid-tight arrangement (1) a means for withdrawing a sample from a body of the fluid, (2) an aging conduit for passing the sample in turbulent flow without backmixing, said conduit having a length and shape adapted to maintain the sample therein for a time substantially equal to the time needed for passage of the main body of the fluid between the sampling means and a permeable particulate medium; (3) a permeable particulate test medium; and (4) a means for passing at least a portion of the aged fluid sample through the permeable particulate test medium. Optionally, the apparatus also includes a means for adding a treating material to the fluid stream, a means for filtering the fluid stream, and/or a means for passing a conditioning fluid through the apparatus before and/or after the test.

BRIEF DESCRIPTION OF THE DRAWING

The drawing is a schematic flow diagram of the preferred embodiment of the invention.

DETAILED DESCRIPTION OF THE INVENTION

Referring now to the drawing, a hot pressurized fluid, such as a geothermal brine, an enhanced oil recovery fluid, or the like, passes from source 2 which can be a place of mixing or prior utilization, such as a heat exchanger, through conduit 4 towards location 6, a place of disposal or further utilization. Generally at location 6 the fluid is passed into a permeable particulate medium, such as an injection well penetrating a permeable subterranean formation. Somewhere along conduit 4, a portion of the fluid is withdrawn via sampling conduit 8, passed through booster pump 10, and sent into the flow test apparatus of this invention. Preferably, the sampling is carried out by continuously withdrawing a fluid sample stream from the main body of the fluid flowing through conduit 4.

A first portion of this sample of fluid usually is passed via conduit 12 to one or the other of filtering means 14 and 16 to remove particulate matter from the fluid. Filtering means 14 and 16 are preferably swing membrane filters.

The filtered fluid flows through conduit 18 to a flow control device 20, such as an orifice plate, the flow rate therethrough being measured and controlled by flow recorder controller 22. Then the sample stream preferably is again divided, a fraction passing through conduit 24 and flow control device 26, the flow rate therethrough being measured and controlled by flow recorder controller 28. As the remaining components of the test apparatus require relatively less volume of test fluid than do filters 14 and 16, the remainder of the first portion of the fluid sample passes through conduits 24 and 30 and is reinjected into conduit 4 at a point downstream of conduit 8.

From flow control device 26, the fluid passes first through conduit 32 and then aging conduit 34, the latter of which is enclosed in an aging tank 36 and is preferably of a coiled, or serpentine configuration to promote tubulent flow therein. Turbulent flow prevents backmixing of the stream and thereby ensures that the sample stream will be of uniform age, that is, unmixed with portions having less or greater age at any given point. The flow rate through aging conduit 34 as well as the diameter and length of aging conduit 34 are preferably controlled so that the residence time of the sampled fluid in the flow test apparatus substantially corresponds to the time required for the main body of the fluid to flow from the point of sampling at conduit 8 to location 6 via conduit 4. The rate of fluid flow through aging conduit 34 is also preferably regulated so that the fluid passing therethrough is in turbulent flow.

A first portion of the fluid from aging conduit 34 then flows from aging tank 36 via conduit 38 into a means for measuring the effect of flow of the fluid through a permeable particulate test medium 42 contained within confining vessel 40. Permeable particulate test medium 42 is typically a core, most preferably a cylindrical core of a subterranean reservoir or a core fashioned of a synthetic solid material, such as fused aluminum oxide particles, having flow characteristics which correspond to those of the permeable particulate medium at location 6. To simulate the effect of passing a fluid into a subterranean reservoir, such as reinjecting spent geothermal brine into a geothermal reservoir, it is most preferred that the core be removed from the reservoir actually being tested, or from one having similar chemical composition and flow characteristics, such as permeability and porosity. For instance, if the permeability of the reservoir rock is derived primarily from natural fractures rather than from permeability in the rock matrix, such fractures can be duplicated or simulated in the cores used in the test apparatus. Plugging of the fractures by injection of the reservoir fluid can then be evaluated by passing the test fluid through the core under reservoir conditions of temperature and pressure.

Confining vessel 40 usually includes means for maintaining permeable test medium 42 at a constant temperature and pressure, preferably at the temperature and pressure existing within the permeable particulate medium at location 6. Most preferably, containing vessel 40 is a Hassler sleeve, a well known device which accommodates a cylindrically shape core within a flexible envelope so that the core is subjected to lateral or radial pressure of sufficient magnitude to permit passage of test fluid through the core in an axial direction only, that is, from end to end. Alternatively, the core may be encased within a sleeve of a plastic material which hardens to form an inflexible envelope to achieve the same result.

The pressure drop across permeable particulate medium 42 is usually measured by pressure drop recorder 44, which makes a continuous recording of pressure. An increase in pressure drop across test medium 42 typically indicates that precipitates from the fluid or products from chemical reaction of the fluid with the test medium have been formed.

At the conclusion of the test, permeable particulate test medium 42 can be removed from confining vessel 40 and examined to observe any change that may have occurred within the permeable particulate test medium, such as formation of precipitates or other reaction products. Any precipitates or reaction products found may be identified by analysis so that appropriate steps can be taken to prevent plugging of the permeable particulate medium at location 6. For example, conventional treating compounds can be added to the sample stream to determine the effectiveness of the compounds for counteracting precipitation in the permeable particulate medium at location 6.

Also, at the conclusion of the test, filters 14 and 16, if used, can be examined to determine the nature of any particulate matter contained in the test fluid as sampled. Preferably, filters 14 and 16 are positioned ahead of aging conduit 34 so that by comparing the change in flow rate across permeable particulate medium 42 using filtered and unfiltered test fluid, the extent of precipitates forming in the test fluid during aging can be determined.

After passage through permeable test medium 42 housed in confining vessel 40, the fluid next passes serially through conduit 46, through cooler or refrigerator unit 48, where the temperature is conveniently reduced below the boiling point of the fluid at atmospheric pressure, and through conduit 50 to waste container 52. Periodically, a sample of the fluid flowing through conduit 50 can be withdrawn via conduit 54 to a volume-measuring means 56, such as a graduated container, to determine the volume of fluid flowing through permeable particulate medium 42 in a unit period of time.

The remaining portion of the fluid flowing through conduit 38 is withdrawn via conduit 58 and returned via conduits 185 and 166 to conduit 4 at a location downstream of conduit 8. During use, a sample of this remaining portion of the aged sample stream can be withdrawn via conduit 60 for further examination and collected via a sampling means, such as sample bomb 62, and then sent to conduit 185 via conduit 63. By way of the sampling means, the effect on the flow of filtered fluid through the test apparatus can be determined. Also means are thereby provided for obtaining samples of the test fluid for further examination. Usually, most of the fluid stream withdrawn for testing via conduit 58 does not pass through conduit 60 into sample bomb 62, but is returned to the main fluid stream via conduits 185 and 166.

A second portion of the fluid passing through conduit 12 is passed by way of conduit 162, valve 156 and conduit 64 to flow control device 66 controlled by flow recorder controller 68. Optionally, a treating material can be pumped from supply 70 by way of conduit 72 and blended under pressure into the fluid prior to its reaching flow control device 66. In a manner similar to that described above, this fluid subsequently flows serially through conduit 74, aging conduit 76 situated in aging tank 78, conduit 80, confining vessel 82, permeable particulate test medium 84 monitored by pressure drop recorder 86, conduit 88, cooler 90, conduit 92, to waste container 52. Optionally, liquid may be withdrawn from conduit 92 through conduit 94 to volume-measuring device 96, or from conduit 80 through conduits 178 and 98, sample bomb 100, and conduits 102 and 180 to conduit 4. With this second portion of the sampled fluid, the effect of the flow through the test apparatus of an unfiltered fluid, which may or may not contain a treating material, is determined.

Similarly, a third portion of the fluid passing through conduit 12 is passed serially by way of conduit 162, valve 156, and conduit 104 to flow control device 106, which is controlled by flow recorder-controller 108. In a manner similar to that described above, the fluid subsequently flows through conduit 110, aging conduit 112 situated in aging tank 114, conduit 116, confining vessel 118, permeable particulate test medium 120 monitored by pressure drop recorder 122, conduit 124, cooler 126, conduit 128 to waste container 52. Optionally, liquid may be withdrawn from conduit 128 through conduit 130 to volume-measuring device 132, or from conduit 116 through conduit 134, sample bomb 136, conduits 138, 164, and 166 to conduit 4. With this third portion of the sample fluid, the effect of the flow of an unfiltered fluid through the test apparatus can be determined.

Alternatively, this section of the test apparatus containing the third portion of the sample fluid can be used to preflush and/or purge the entire apparatus at the beginning and end of the test period with a conditioning fluid. When it is desired to preflush or purge the entire apparatus, the flow of fluid into conduit 12 can be stopped by valves 154 and 156 and a conditioning fluid can be pumped from supply 140 via conduit 142, heater 144 and conduit 146 into conduit 104. In this manner a preflush or purge fluid can optionally be passed through the entire fluid flow apparatus, that is, through permeable particulate media 42, 84 and 120 and the equipment associated therewith, or through all of the apparatus except for permeable particulate media 42, 84 and 120. The preflush and afterflush fluid typically differ from the test fluid in composition and/or physical properties, or are under conditions such as temperature and pressure as desired by the practitioner to prepare or clean the apparatus. For instance, in testing hot pressurized fluids such as geothermal brines likely to form deposits at various locations throughout the test equipment, it is sometimes necessary to carefully prepare the test equipment to handle the fluid before the test and/or to purge or flush the test equipment of the fluid at the conclusion of the test. Heated preflush can be used to get the various pieces of the test equipment up to the temperature of the test fluid before introduction of the test fluid. Danger of precipitating a constituent of the test fluid within the test apparatus due to the fluid contacting a relatively cold surface at the start of the test period is thereby decreased. On the other hand, a heated purge or flush passed through the apparatus at the conclusion of the test washes the test fluid out of the test apparatus and eliminates or minimizes the danger of precipitating a constituent of the test fluid within the test apparatus due to cooling or evaporation when the test equipment is drained. The purge fluid is preferably passed through the test equipment after the permeable test medium has been removed so as to avoid altering the results of the experiment by washing away deposits from the test medium left therein.

In order to help maintain the temperature of the test fluid during its residence in aging conduits 34, 76 and 112, a heating means is provided, such as a heated heat exchange medium, for example a silicone, and is pumped from supply container 148 through conduit 150, circulated through aging tanks 36, 78 and 114 via conduits 170, 172 and 174, and then returned to supply container 148 by way of conduit 152.

To further maintain the test fluid at a substantially uniform temperature throughout the test apparatus, it is preferred to enclose flow control devices 20, 26, 66 and 106, aging tanks 36, 78 and 114 and their various associated equipment within a temperature control means 158, such as an electrically heated oven. Similarly, permeable particulate media 42, 84 and 120 are enclosed within a temperature control means 160, which is preferably an electrically heated oven. Most preferably, the test fluid is maintained at a temperature substantially corresponding to the temperature of the main body of the fluid during passage between the sampling point and the point of injection into a permeable particulate medium.

Valves 154 and 156 control the relative amounts of fluid flowing through conduits 12 and 64. Numerous other valves (not shown) are stragetically placed throughout the apparatus to direct the fluid flow in the desired manner.

The invention is further described by the following example which is illustrative of a specific mode of practicing the invention and is not intended as limiting the scope of the invention as defined by the appended claims.

EXAMPLE 1

It is desired to measure the damage to reservoir permeability caused by reinjection of spent geothermal brine produced from a California geothermal reservoir back into the same reservoir. The produced brine, having a temperature of 350° F. and a pressure of 200 p.s.i.g., is to be reinjected via an injection well at the rate of 500,000 pounds per hour at a depth of 5,000 feet in the geothermal reservoir. It is calculated that it takes 15 minutes for the injected brine to reach the face of the reservoir from the point of sampling for the flow test.

The permeable particulate medium used is a one inch diameter Berea sandstone cylindrical core 3 inches long. The core is confined within a Hassler sleeve, which maintains the temperature at 350° F. and the pressure at 200 p.s.i.g. To bring the test apparatus up to approximately the temperature of the test fluid before introduction of the test fluid and to eliminate microorganisms, the apparatus is preflushed with 25 gallons of an aqueous solution maintained at a temperature of 350° F. and a pressure of 200 p.s.i.g. and containing a concentration of 25 ppm of the fungicide "Dowicide F" manufactured by Dow Chemicals. The preflush fluid is pumped through the apparatus at a rate of ½ gallon per minute.

Next, a 10 gallon per minute sample of the geothermal brine is continuously withdrawn from the conduit carrying the brine to the injection well. A portion of the sample stream is passed through an isothermal aging conduit maintained at a temperature of 350° F. under conditions of turbulent flow and then is passed through the Berea sandstone core at an initial rate of 300 grams per minute, slowing gradually until the core plugs up and will no longer pass fluid. Residence time in the isothermal aging conduit is such that the time from withdrawal of a portion of the fluid sample into the test apparatus until that portion of the fluid sample reaches the Berea core is approximately 15 minutes. During the time the fluid sample is passed through the Berea core, the pressure drop across the core is maintained substantially constant at about 10 p.s.i.g. After about two hours, the core is plugged. The test is then terminated, and the test apparatus is purged of the test fluid by pumping therethrough 25 gallons of the aqueous preflush solution at a temperature of 350° F. and a pressure of 200 p.s.i.g. The purge fluid is not passed through the Berea core. The Berea core is then removed from the test apparatus and examined to determine the effect of the test fluid thereon.

The principal advantage of the invention is that a permeable test medium which is chosen to be similar in chemical composition and/or flow characteristics to a permeable particulate medium to be used in an industrial operation, such as a core taken from a reservoir intended to undergo injection of fluids, can be used to predict or determine the damage to permeability, or other change, that will be caused by large-scale injection of fluids.

This invention offers the additional advantage of aid in controlling plugging in the permeable medium, such as is caused by formation of precipitates during injection of fluids. A particularly common and expensive occurrence of this phenomenon results from reinjection of spent brines into geothermal reservoirs. When increased pressure drop or a slowing flow rate through the test medium during simultaneous injection indicates that plugging of the reservoir is occurring, the effect of additives to the test fluid upon the test medium can be evaluated to determine how best to control or reverse plugging in the reservoir. Thus, plugging can be detected and steps taken to correct it without the need for costly downtime at the well.

While particular embodiments of the invention have been described in the foregoing specification, it will be understood, of course, by those skilled in the art that the invention is not limited thereto since many modifications can be made, and it is intended to include within the invention such modifications as are within the scope of the invention as defined by the following claims.

I claim:

1. An apparatus for predicting the effect of the flow of a fluid through a permeable particulate medium comprising:
    (a) sampling means for withdrawing from a body of the fluid a sample stream;
    (b) an aging conduit in fluid-tight communication to the sampling means for passing the sample stream therethrough in turbulent flow without substantial backmixing, said conduit having a length and shape adapted to retain the sample stream therein for a time substantially equal to the time required for the body of the fluid to traverse the distance between the sampling means and the permeable particulate medium;
    (c) a permeable particulate test medium in fluid-tight communication with the aging conduit;
    (d) means for flowing an aged sample stream recovered from the aging conduit through the permeable particulate test medium; and
    (e) means for measuring the effect of flow of the aged sample stream through the permeable particulate test medium.

2. The apparatus defined in claim 1 wherein the means for measuring the effect of flow comprises a means for measuring the pressure drop across the test medium.

3. The apparatus defined in claim 1 wherein the means for measuring the effect of flow comprises a means for measuring the flow rate through the test medium.

4. The apparatus defined in claim 1 wherein the aging conduit is enclosed in an aging tank.

5. The apparatus defined in claim 4 wherein the aging tank is provided with means to maintain the fluid sample stream under elevated substantially isothermal conditions.

6. The apparatus defined in claim 5 wherein the means for maintaining the fluid sample stream at elevated, substantially isothermal conditions comprises an electrically heated oven which encloses said aging tank.

7. The apparatus defined in claim 5 wherein the means for maintaining the fluid sample stream at elevated, substantially isothermal conditions comprises a circulating heat exchange medium.

8. The apparatus defined in claim 1 wherein the aging conduit has a coiled configuration.

9. The apparatus defined in claim 1 including means for filtering the sample stream before passing the same through the aging conduit.

10. The apparatus defined in claim 9 wherein the filtering means includes a membrane filter.

11. The apparatus defined in claim 1 further comprising means for adding a treating material to the sample stream before passing the sample stream through the aging conduit.

12. The apparatus defined in claim 1 further comprising a flow control device to regulate the rate of flow of the sample stream through the aging conduit.

13. The apparatus defined in claim 12 wherein the flow control device comprises an orifice plate.

14. The apparatus defined in claim 12 wherein the flow control device comprises a flow recorder controller.

15. The apparatus defined in claim 1 further comprising means for sampling the aged sample stream.

16. The apparatus defined in claim 15 wherein the means for sampling the aged sample stream comprises a sample bomb.

17. The apparatus defined in claim 1 further comprising means for measuring the pressure drop across the permeable particulate test medium.

18. The apparatus defined in claim 1 further comprising a volume-measuring means to determine the volume of the aged sample flowing through the permeable particulate test medium in a unit period of time.

19. The apparatus defined in claim 18 further comprising means to cool the sample before passing to the volume-measuring means.

20. The apparatus defined in claim 1 wherein the permeable particulate test medium comprises a core taken from a subterranean reservoir.

21. The apparatus defined in claim 1 wherein the permeable particulate medium comprises a permeable core of fused solid material.

22. The apparatus defined in claim 21 wherein the fused solid material is particles of aluminum oxide.

23. The apparatus defined in claim 1 wherein the permeable particulate test medium is provided with means for maintaining the aged sample stream at an elevated temperature and pressure during passage through the test medium.

24. The apparatus defined in claim 1 wherein means is provided for flowing through the apparatus a conditioning fluid stream having properties different than those of the sample stream.

25. The apparatus defined in claim 1 wherein means is provided for flowing through the apparatus a conditioning fluid stream at conditions of temperature and pressure sufficient to substantially prevent formation of precipitates in the apparatus.

26. An apparatus for determining the effect of reinjecting a geothermal brine at an elevated temperature and pressure into a permeable subterranean formation comprising:
   (a) sampling means for withdrawing a continuous sample stream from a main body of the geothermal brine flowing through a conduit towards a permeable subterranean reservoir penetrated by a well;
   (b) a plurality of aging conduits in fluid-tight communication with the sampling means for passing separate portions of the sample stream in turbulent flow without substantial back-mixing, each aging conduit having a length and shape adapted to retain the sample stream therein for a time substantially equal to the time required for the main body of the geothermal brine to traverse the distance between the sampling means and the subterranean reservoir;
   (c) a plurality of aging tanks, each of which contains one of the aging conduits, the aging tanks being adapted to maintain the portion of the sample stream passed therethrough at elevated, substantially isothermal conditions;
   (d) a permeable particulate test medium in fluid-tight communication with each aging conduit for passing therethrough a portion of the aged sample stream recovered from the aging conduit;
   (e) means in fluid-tight communication with the permeable particulate test medium for maintaining the test medium at an elevated temperature and pressure; and
   (f) means in fluid-tight communication with the test medium for measuring the effect of flow of the portion of the aged sample stream therethrough.

27. The apparatus defined in claim 26 wherein the means for measuring the effect of flow comprises a means for measuring the rate of flow through the test medium.

28. The apparatus defined in claim 26 wherein the means for measuring the effect of flow comprises a means for measuring the pressure drop across the test medium.

29. An apparatus as defined in claim 26 which apparatus further comprises:
   (g) means for filtering a portion of the sample stream located ahead of at least one but not all of the aging conduits;
   (h) means for collecting a sample of the aged sample stream recovered from test medium (d);
   (i) means for cooling at least one portion of the sample stream recovered from the permeable test medium in step (f);
   (j) means for admixing a treating material into at least one portion of the sample stream before passage through the permeable particulate test medium;
   (k) means for flowing throughout the apparatus, a conditioning stream having physical properties different from those of the fluid sample stream; and
   (l) means for collecting a portion of the aged sample stream recovered from said cooling means (i).

30. An apparatus as defined in claim 29 further comprising means for maintaining the conditioning stream at a temperature and pressure effective for minimizing formation of precipitates from the sample stream.

31. A method for determining the effect of the flow of a fluid at elevated temperature and pressure through a permeable particulate medium, which method comprises:
 (a) continuously withdrawing a sample stream from the main body of the fluid at a sampling point;
 (b) passing the main body of the fluid into a permeable particulate medium;
 (c) passing the sample stream through an aging conduit under conditions of turbulent flow without substantial back-mixing to provide a sample stream having a uniform age, which age is substantially equal to the time required for the main body of the fluid to traverse the distance between the sampling point and the permeable particulate medium;
 (d) passing a uniformly aged sample stream from step (c) through a permeable particulate test medium; and
 (e) determining the effect of passage of the uniformly aged sample stream through the permeable particulate test medium in step (d) so as to predict the effect of passage of the body of the sample stream through the permeable particulate medium in step (b).

32. The method defined in claim 31 wherein the aged sample stream contained in the aging conduit is maintained at substantially the temperature and pressure of the main body of the fluid and the permeable particulate test medium is maintained at substantially the temperature and pressure of the permeable particulate medium.

33. The method defined in claim 32 wherein at least one portion of the sample stream is passed through a means for filtering before passage through the aging conduit.

34. The method defined in claim 33 wherein the means for filtering comprises a membrane filter.

35. The method defined in claim 31 further comprising admixing treating material with at least one portion of the fluid sample before passage through the permeable particulate test medium so as to alter flow conditions through the test medium.

36. The method defined in claim 31 wherein the fluid sample stream is passed at a controlled rate through the aging conduit.

37. The method defined in claim 31 wherein an aged sample recovered from the aging conduit is withdrawn before the remainder of the aged sample stream is passed through the permeable particulate test medium and the effect of aging step (c) upon the sample stream is determined by analysis of the aged sample.

38. The method defined in claim 31 wherein the effect of the aged sample stream upon the permeable particulate test medium is determined in step (e) by measuring the pressure drop across the permeable particulate test medium.

39. The method defined in claim 31 wherein the effect of the sample upon the permeable particulate medium is determined in step (e) by comparing the volumes of the sample stream passed through the permeable particulate test medium in given periods of time.

40. The method defined in claim 31 wherein the permeable particulate test medium comprises a core taken from a subterranean formation and the permeable particulate medium is a subterranean reservoir.

41. The method defined in claim 40 wherein the core is taken from the subterranean reservoir.

42. The method defined in claim 41 wherein the subterranean reservoir is a geothermal reservoir and the fluid is a spent geothermal brine.

43. The method defined in claim 31 wherein the permeable particulate test medium comprises a fused solid material.

44. The method defined in claim 43 wherein the fused solid material comprises particles of aluminum oxide.

45. The method defined in claim 31 wherein the temperature of the sample fluid within the aging conduit is maintained substantially isothermal.

46. The method defined in claim 31 wherein the aged sample stream during passage through the permeable particulate test medium is maintained at substantially the temperature and pressure prevailing in the permeable particulate medium.

47. The method defined in claim 31, which method further comprises passing a conditioning fluid stream through the apparatus ahead of the sample stream so as to prevent formation of precipitates from the sample stream during passage therethrough.

48. A method for determining the effect of reinjecting a geothermal brine into a geothermal reservoir at an elevated temperature and pressure comprising:
 (a) continuously withdrawing a sample stream from the body of a stream of geothermal brine flowing through a conduit into said geothermal reservoir;
 (b) continuously reinjecting the body of the geothermal brine into the geothermal reservoir;
 (c) passing at least a portion of the sample stream through an aging conduit under conditions of turbulent flow without substantial back-mixing and without substantial formation of precipitates therefrom so as to provide a sample having a uniform age substantially equal to the time required for the body of the geothermal brine to pass between the sampling point and the subterranean formation;
 (d) passing a uniformly aged sample stream from step (c) axially through a core comprising a permeable particulate test medium;
 (e) maintaining the temperature and the pressure of the sample stream at substantially the temperature and pressure of the main body of the brine during passage between the sampling point and the point of entry into the geothermal formation; and
 (f) predicting the effect of passage of the main body of the brine through the geothermal formation by determining the effect of passage of the sample stream through the permeable particulate test medium.

49. The method of claim 48 wherein the permeable particulate test medium comprises fused solid particles.

50. The method of claim 49 wherein the solid particles are aluminum oxide.

51. The method of claim 48 wherein the permeable particulate test medium is a subterranean formation.

52. The method of claim 51 wherein the subterranean formation is the geothermal reservoir.

* * * * *